United States Patent [19]

Cattani

[11] Patent Number: 5,002,486

[45] Date of Patent: Mar. 26, 1991

[54] CONTROL DEVICE FOR SUCTION SYSTEMS USED IN DENTISTRY

[75] Inventor: Augusto Cattani, Parma, Italy

[73] Assignee: Officine Augusto Cattani & C. S.p.A., Parma, Italy

[21] Appl. No.: 283,314

[22] Filed: Dec. 12, 1988

[30] Foreign Application Priority Data

Mar. 30, 1988 [IT] Italy .............................. 40049 A/88

[51] Int. Cl.[5] .............................................. A61C 17/06

[52] U.S. Cl. ......................................... 433/91; 433/95

[58] Field of Search ....................... 433/95, 91, 92, 28; 137/552.7; 604/22, 118, 119, 120

[56] References Cited

U.S. PATENT DOCUMENTS 3,482,313 12/1969 Stram .................................. 433/92
3,808,449 4/1974 Peruglia .............................. 137/557
4,308,011 12/1981 Liefke ................................. 433/28
4,496,342 1/1985 Banko ................................. 604/31

*Primary Examiner*—Cary E. Stone
*Attorney, Agent, or Firm*—Darby & Darby

[57] ABSTRACT

The device forms part of an automatic control facility by which the water-primed oral suction pump in dental surgery equipment is protected from the effects of low water pressure and power cuts; the efficiency of control is improved by the inclusion of timers (7, 9) that ensure continued operation of the pump and its inlet valve in the event that fluctuations in the water pressure and electrical power levels happen to be of a momentary order.

5 Claims, 1 Drawing Sheet

13
12
9
8
3
7
6
2
1
11
10
4
10
11
5

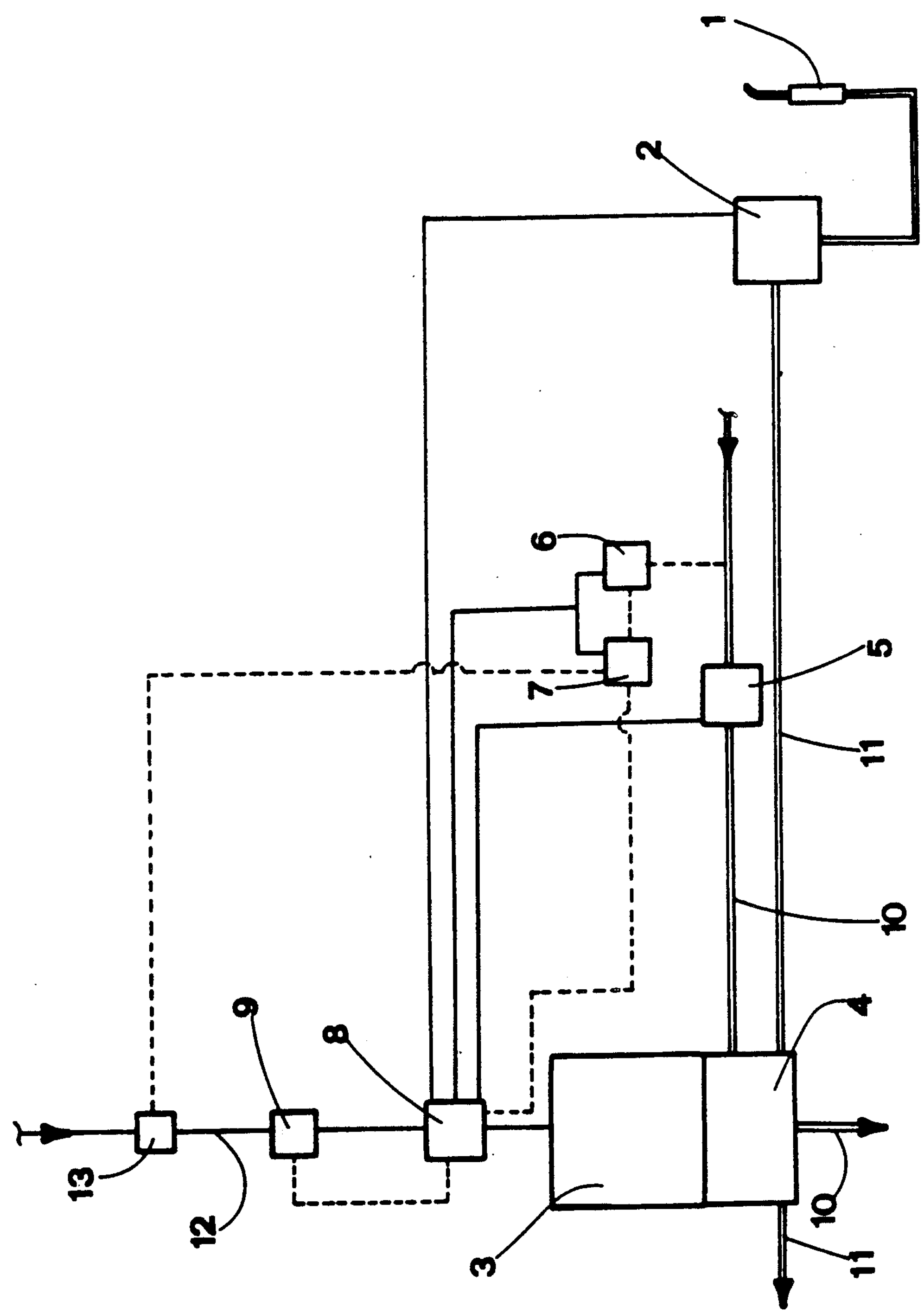
1
2
6
7
5
11
10
4
9
8
13
12
3
10
11

CONTROL DEVICE FOR SUCTION SYSTEMS USED IN DENTISTRY

BACKGROUND of the INVENTION

The invention relates to a control device for the liquid stream suction sYstems used in dentistry. In suction systems of the type in question, where evacuated fluids are drawn into a stream of liquid, the liquid most widely utilized is water from the domestic main. During normal operation, water is drawn into the impeller of a pump set in rotation by an electric motor; however, it happens in such systems that if no water enters the system, or even if the pressure of the water supply is simply too low, the pump will deteriorate rapidly.

This being the case, the system will generally be provided with a pressure switch designed to sense the pressure level of the water supply, and in the event of the level falling below a given threshold, to generate a signal that switches off the system; in most instances, such a switch will operate by cutting off the electrical power supply to the motor and actuating a solenoid valve to close the water supply inlet.

One of the disadvantages of these systems is that the opening movement of the solenoid valve induces hammering in the water supply line, setting up pressure waves that are picked up by the pressure switch and have the effect of triggering a rapid succession of on and off movements during the transition from standstill to normal operation of the suction circuit. The result is that one has a deterioration of the various components producing electrical contact, due to the surges in current that accompany the rapidly alternating on and off movements preceding steady operation.

Hammering-induced pressure waves also occur in the event of a sudden drop or cut in the electrical power supply; furthermore, critical pressure levels in the water supply itself can cause the entire system to vibrate.

The object of the invention is to overcome the drawbacks described above by providing a control device which will shut off the suction system in the event that water supply pressure should either become insufficient or fail altogether, and at the same time, remain unaffected by sudden variations in pump inlet pressure, in particular when produced by hammering.

SUMMARY OF THE INVENTION

The stated object is achieved with a control device according to the invention, which is intended for application to suction systems of the type using a stream of liquid generated by a motor driven rotary pump the inlet of which is controlled by a solenoid operated on-off valve.

The device disclosed comprises a driver module in receipt of a.c. power and designed to supply the various components of the device with electrical power at the appropriate voltage, and a pressure switch designed to sense water pressure through the pump inlet line and emit a control signal whenever the pressure level happens to drop below a given threshold.

According to the present invention, use is made of a timer, of conventional embodiment, piloted by the control signal emitted from the pressure switch and designed to generate a signal that will shut off the system in the event that the duration of the control signal exceeds a prescribed time limit.

BRIEF DESCRIPTION OF THE DRAWINGS

The invention will now be described in detail, by way of example, with the aid of the accompanying drawing, which provides a schematic illustration of one possible embodiment.

DESCRIPTION OF THE PREFERRED EMBODIMENTS

The control device according to the invention is designed for integration into a suction system of the type wherebY fluids are drawn into a stream of liquid set in motion by a rotary pump 4: the pump is driven by an electric motor 3 and takes in water from the domestic main through a pipeline 10, which is governed by a solenoid operated on-off valve 5. Negative pressure created by the pump 4 operates in conjunction with an air line 11 to generate suction through a cannula tube 1 which, in the majority of the dental surgery equipment conventionally in use, is connected to the pump 4 through a conveniently placed stand or table denoted 2.

The various electrical components of the system are wired into a conventional electronic power module, or driver 8, in receipt of alternating current from the electrical power supply line 12, which it duly converts and supplies to the different components at the requisite voltage.

The control device disclosed comprises a pressure switch 6, the purpose of which is to sense the pressure level of the water internally of the inlet pipeline 10 and emit an electrical signal whenever the level falls below a prescribed threshold. The device also comprises a first timer 7, into which the control signal from the pressure switch 6 is cascaded, and which in turn produces an output signal serving to shut off the pump 4 whenever the duration of the pressure switch signal exceeds a prescribed time limit; in short, the first timer 7 will trigger shut-off of the system by way of the power module 8 only when one has a marked drop in pressure lasting for longer than, typically, a few seconds. Accordingly, there is no possibility of the pump being shut off in response to the shock waves induced by hammering, which normally subside within the space of approximately one second.

In the example illustrated, the control signal from the first timer 7 is also used to pilot a manually reset circuit breaker 13 wired into the a.c. supply line 12 on the input side of the power module 8; such an expedient provides the additional safeguard that, in the event of the system being shut off due to low water pressure (and in particular, when the supply of water ceases completely), the operator is obliged to intervene directly, i.e. first ensuring that the water supply is restored, then switching the system back on by resetting the circuit breaker manually.

9 denotes a second timer which, in the event of a momentary loss of electrical power, prevents the solenoid valve 5 from closing before a prescribed interval of time has lapsed; accordingly, one avoids any possibility of hammering occasioned by sudden de-energization and re-energization of the valve 5 in response to fluctuations in the a.c. power supply.

Operation of the device will now be described. In systems of the type in question, the suction circuit is activated by removing the tube 1 from its holder 2 to operate a switch and thus pilot operation of the power module 8, which starts up the pump motor 3 and opens the solenoid valve 5, whereupon water is drawn through the pump 4, and suction generated.

In the transition that precedes steady operation, the rush of water into the pipeline 10 produces hammering; the resulting pressure waves are sensed by the pressure switch 6, which generates an output signal with each negative half-period. The train of pulsed signals produced in this way is relayed to the first timer 7, but being of duration typically no longer than one second or less, the system will continue to operate as normal, as a signal shorter than the prescribed time limit is interpreted as constituting no potential disturbance. Accordingly, one avoids the rapid succession of stops and starts that would inevitably occur without the timer 7. In the event of water pressure in the pipeline 10 dropping permanently or failing to register at all, the control signal emitted by the pressure switch 6 becomes continuous, and on exceeding the set time limit (a few seconds, as aforementioned), the first timer 7 generates a signal which, when relayed to the power module 8, will cut off electrical power to the motor 3 and the solenoid valve 5. At the same time, the signal emitted by the first timer 7 is relayed to the circuit breaker 13, and the entire system isolated from the a.c. power supply; at this point, power will only be restored to the system and normal operation resumed once water pressure has been recovered, whereupon the circuit breaker 13 can be reset manually by the operator. Dhould there be a drop in the a.c. supply voltage, the power module 8 will cease to drive the motor 3 and to energize the solenoid valve 5; in the event that the duration of such a drop is less than the prescribed limit (likewise, a few seconds), the second timer 9 prevents immediate de-energization of the solenoid, and the valve 5 will close only if the power cut becomes prolonged beyond the timer setting. Where the drop in voltage is momentary, in fact, the motor will continue rotating under its own inertia and resume normal operation as power is restored, whereas the solenoid valve 5 will be totally unaffected by the fluctuation, thanks to the override effect of the second timer 9.

In the event of a prolonged drop or cut in the a.c. supply, the solenoid valve 5 closes and the motor 3 shuts off, whereupon normal operation will resume as soon as the rated a.c. supply voltage has been restored.

What is claimed:

1. A control device for suction systems of a type using a stream of liquid generated by a motor driven rotary pump, said pump having an inlet for liquid which is controlled by an on-off solenoid valve, comprising:

a driver module for connection to an a.c. power supply and designed to supply the various components respectively of the control device and suction system with electrical power and appropriate voltages during operation of said suction system;

a pressure switch for sensing liquid pressure at the pump inlet and for emitting a control signal when the pressure level drops below a prescribed threshold;

a first timer actuated by the control signal emitted from said pressure switch, said first timer generating a shut off signal in the event that said control signal exceeds a prescribed time limit in duration, said shut off signal deactivating said pump, a second timer operating in response to the voltage level of said a.c. power supply for preventing the solenoid valve from closing before a prescribed interval of time has lapsed, in the event of an interruption in the a.c. power supply.

2. A control device for suction systems of a type using a stream of liquid generated by a motor driven rotary pump, said pump having an inlet for liquid which is controlled by an on-off solenoid valve, comprising:

a driver module for connection to an a.c. power supply and designed to supply the various components respectively of the control device and suction system with electrical power and appropriate voltages during operation of said suction system;

a pressure switch for sensing liquid pressure at the pump inlet and for emitting a control signal when the pressure level drops below a prescribed threshold;

a first timer actuated by the control signal emitted from said pressure switch, said first timer generating a shut off signal in the event that said control signal exceeds a prescribed time limit in duration, said shut off signal deactivating said pump, wherein the control signal actuated a manually reset circuit breaker wired into the a.c. supply line on the input side of the driver module.

3. A control device for suction systems of a type using a stream of liquid generated by a motor driven rotary pump, said pump having an inlet for liquid which is controlled by an on-off solenoid valve, comprising:

electrical means having an input side and an output for powering components of said control device and suction system with appropriate voltages;

a pressure switch for sensing liquid pressure at the pump inlet and for emitting a control signal when the pressure level drops below a prescribed threshold;

a first timer actuated by the control signal emitted from said pressure switch, said first timer generating a shut off signal in the event that said control signal exceeds a prescribed time limit in duration, said shut off signal deactivating said pump.

4. A device as in claim 3, comprising a second timer operating in response to the voltage level at the input side of said electrical means for preventing the solenoid valve from closing before a prescribed interval of time has elapsed in the event of an interruption in power to the electrical means.

5. A device as in claim 3, wherein the control signal actuates a manually reset circuit breaker wired into the input side of the electrical means.

* * * * *